United States Patent
Hsu et al.

(10) Patent No.: US 7,203,535 B1
(45) Date of Patent: Apr. 10, 2007

(54) SYSTEM AND METHOD FOR CLASSIFYING TACHYCARDIA ARRHYTHMIAS HAVING 1:1 ATRIAL-TO-VENTRICULAR RHYTHMS

(75) Inventors: William Hsu, Circle Pines, MN (US); Robert J. Sweeney, Woodbury, MN (US); Eric G. Lovett, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/417,558

(22) Filed: Oct. 13, 1999

Related U.S. Application Data

(63) Continuation-in-part of application No. 09/283,159, filed on Apr. 1, 1999, now Pat. No. 6,179,865.

(51) Int. Cl.
*A61B 5/0402* (2006.01)
(52) U.S. Cl. .................................................. 600/518
(58) Field of Classification Search ............. 600/372, 600/373, 374, 508, 509, 513, 514, 515, 516, 600/518, 519, 521; 607/14
See application file for complete search history.

(56) References Cited

U.S. PATENT DOCUMENTS

| | | | |
|---|---|---|---|
| RE30,387 E | 8/1980 | Denniston, III et al. | |
| 4,515,161 A | 5/1985 | Wittkampf et al. | 128/419 |
| 4,543,963 A | 10/1985 | Gessman | 128/702 |
| 4,572,192 A | 2/1986 | Jackman et al. | 128/419 PG |
| 4,577,634 A * | 3/1986 | Gessman | 128/419 |
| 4,583,553 A | 4/1986 | Shah et al. | 128/704 |
| 4,721,114 A | 1/1988 | DuFault et al. | |
| 4,802,483 A | 2/1989 | Lindgren | 128/419 PG |
| 4,830,006 A | 5/1989 | Haluska et al. | |
| 4,832,038 A | 5/1989 | Arai et al. | |

(Continued)

FOREIGN PATENT DOCUMENTS

EP  0033418 A1  8/1981

(Continued)

OTHER PUBLICATIONS

PTO 2003-5102 Translation of European Patent No. EP 0 879 621 A2; Nigam; Nov. 25, 1998.*

(Continued)

*Primary Examiner*—Robert E. Pezzuto
*Assistant Examiner*—Frances P. Oropeza
(74) *Attorney, Agent, or Firm*—Schwegman, Lundberg, Woessner & Kluth

(57) ABSTRACT

An implantable cardioverter/defibrillator includes a tachycardia detection system that detects one-to-one (1:1) tachycardia, which is a tachycardia with a one-to-one relationship between atrial and ventricular contractions. When the 1:1 tachycardia is detected, the system discriminates ventricular tachycardia (VT) from supraventricular tachycardia (SVT) based on analysis of a cardiac time interval. Examples of the cardiac time interval include an atrioventricular interval (AVI) and a ventriculoatrial interval (VAI). A template time interval is created during a known normal sinus rhythm. The system measures a tachycardia time interval after detecting the 1:1 tachycardia, and indicates a VT detection if the tachycardia time interval differs from the template time interval by at least a predetermined percentage of the template time interval.

15 Claims, 7 Drawing Sheets

U.S. PATENT DOCUMENTS

| | | | |
|---|---|---|---|
| 4,838,278 A | 6/1989 | Wang et al. ................ 128/697 |
| 4,860,749 A * | 8/1989 | Lehmann ..................... 128/419 |
| 4,917,115 A * | 4/1990 | Flammang et al. ......... 128/419 |
| 4,920,965 A | 5/1990 | Funke et al. .......... 128/419 PG |
| 4,924,875 A | 5/1990 | Chamoun |
| 4,945,909 A | 8/1990 | Fearnot et al. |
| 5,000,189 A | 3/1991 | Throne et al. ............... 128/702 |
| 5,020,540 A | 6/1991 | Cahmoun ................... 128/696 |
| 5,107,850 A | 4/1992 | Olive ........................ 128/705 |
| 5,184,615 A | 2/1993 | Nappholz et al. |
| 5,193,535 A | 3/1993 | Bardy et al. ............. 128/419 D |
| 5,193,550 A | 3/1993 | Duffin ........................ 129/697 |
| 5,205,283 A | 4/1993 | Olson |
| 5,207,219 A | 5/1993 | Adams et al. .......... 128/419 D |
| 5,228,438 A | 7/1993 | Buchanan ............. 128/419 PG |
| 5,240,009 A | 8/1993 | Williams .................... 128/702 |
| 5,243,980 A * | 9/1993 | Mehra ............................ 607/6 |
| 5,253,644 A | 10/1993 | Elmvist ....................... 607/14 |
| 5,255,186 A | 10/1993 | Steinhaus et al. ........... 364/413 |
| 5,273,049 A | 12/1993 | Steinhaus et al. |
| 5,275,621 A | 1/1994 | Mehra ........................... 607/5 |
| 5,280,792 A | 1/1994 | Leong et al. ............... 128/702 |
| 5,282,836 A | 2/1994 | Kreyenhagen et al. |
| 5,284,491 A | 2/1994 | Sutton et al. |
| 5,291,400 A | 3/1994 | Gilham |
| 5,292,341 A | 3/1994 | Snell |
| 5,292,348 A | 3/1994 | Saumarez et al. ............. 607/5 |
| 5,311,874 A | 5/1994 | Baumann et al. ........... 128/705 |
| 5,312,445 A | 5/1994 | Nappholz et al. .............. 607/9 |
| 5,312,452 A | 5/1994 | Salo |
| 5,313,953 A | 5/1994 | Yomtov et al. |
| 5,327,900 A * | 7/1994 | Mason et al. ............... 128/705 |
| 5,330,504 A | 7/1994 | Somerville et al. |
| 5,331,966 A | 7/1994 | Bennett et al. |
| 5,334,220 A | 8/1994 | Sholder |
| 5,342,402 A | 8/1994 | Olson et al. .................... 607/5 |
| 5,350,406 A | 9/1994 | Nitzsche et al. .............. 607/14 |
| 5,350,409 A | 9/1994 | Stoop et al. |
| 5,351,696 A | 10/1994 | Riff et al. ................... 128/702 |
| 5,356,425 A | 10/1994 | Bardy et al. |
| 5,360,436 A | 11/1994 | Alt et al. |
| 5,366,487 A | 11/1994 | Adams et al. ................. 607/5 |
| 5,370,125 A | 12/1994 | Mason et al. ............... 128/705 |
| 5,379,776 A | 1/1995 | Murphy et al. |
| 5,383,910 A * | 1/1995 | den Dulk ..................... 607/14 |
| 5,387,229 A | 2/1995 | Poore |
| 5,391,189 A | 2/1995 | van Krieken et al. |
| 5,395,397 A | 3/1995 | Lindgren et al. .............. 607/9 |
| 5,400,795 A | 3/1995 | Murphy et al. |
| 5,400,796 A | 3/1995 | Wecke ........................ 128/705 |
| 5,403,352 A | 4/1995 | Rossing |
| 5,411,031 A | 5/1995 | Yomtov |
| 5,411,524 A | 5/1995 | Rahul |
| 5,411,531 A | 5/1995 | Hill et al. |
| 5,417,714 A | 5/1995 | Levine et al. .................. 607/9 |
| 5,431,693 A | 7/1995 | Schroeppel |
| 5,447,519 A | 9/1995 | Peterson ........................ 607/5 |
| 5,456,261 A | 10/1995 | Luczyk |
| 5,458,620 A | 10/1995 | Adams et al. |
| 5,458,623 A | 10/1995 | Lu et al. ....................... 607/28 |
| 5,462,060 A | 10/1995 | Jacobson et al. ........... 128/702 |
| 5,464,433 A | 11/1995 | White et al. |
| 5,466,245 A | 11/1995 | Spinelli et al. |
| 5,474,574 A | 12/1995 | Payne et al. |
| 5,476,482 A * | 12/1995 | Lu ................................ 607/9 |
| 5,480,412 A | 1/1996 | Mouchawar et al. |
| 5,480,413 A | 1/1996 | Greenhut et al. |
| 5,486,198 A | 1/1996 | Ayers et al. .................... 607/5 |
| 5,487,752 A | 1/1996 | Salo et al. |
| 5,487,754 A | 1/1996 | Snell et al. |
| 5,496,350 A | 3/1996 | Lu ................................ 607/14 |
| 5,503,159 A | 4/1996 | Burton |
| 5,507,782 A | 4/1996 | Kieval et al. |
| 5,507,784 A | 4/1996 | Hill et al. |
| 5,514,163 A | 5/1996 | Markowitz et al. |
| 5,520,191 A | 5/1996 | Karlsson et al. |
| 5,522,850 A | 6/1996 | Yomtov et al. |
| 5,522,859 A | 6/1996 | Stroebel et al. |
| 5,527,347 A | 6/1996 | Shelton et al. |
| 5,534,016 A | 7/1996 | Boute |
| 5,542,430 A | 8/1996 | Farrugia et al. ............ 128/705 |
| 5,545,186 A | 8/1996 | Olson et al. |
| 5,549,641 A | 8/1996 | Ayers et al. |
| 5,551,427 A | 9/1996 | Altman ....................... 128/642 |
| 5,560,368 A | 10/1996 | Berger |
| 5,560,369 A | 10/1996 | McClure et al. |
| 5,560,370 A | 10/1996 | Verrier et al. |
| 5,571,144 A | 11/1996 | Schroeppel |
| 5,584,864 A | 12/1996 | White |
| 5,584,867 A | 12/1996 | Limousin et al. |
| 5,591,215 A | 1/1997 | Greenhut et al. |
| 5,605,159 A | 2/1997 | Smith et al. ................. 128/702 |
| 5,609,158 A | 3/1997 | Chan .......................... 128/705 |
| 5,626,620 A | 5/1997 | Kieval et al. |
| 5,626,623 A | 5/1997 | Kieval et al. |
| 5,628,326 A | 5/1997 | Arand et al. |
| 5,645,070 A | 7/1997 | Turcott ....................... 128/702 |
| 5,676,153 A | 10/1997 | Smith et al. |
| 5,682,900 A | 11/1997 | Arand et al. |
| 5,685,315 A | 11/1997 | McClure et al. |
| 5,690,689 A | 11/1997 | Sholder |
| 5,697,377 A | 12/1997 | Witkampf .................... 128/696 |
| 5,704,365 A | 1/1998 | Albrecht et al. |
| 5,713,367 A | 2/1998 | Arnold et al. ............... 128/704 |
| 5,713,930 A | 2/1998 | van der Veen et al. |
| 5,718,242 A | 2/1998 | McClure et al. |
| 5,730,141 A | 3/1998 | Fain et al. |
| 5,730,142 A | 3/1998 | Sun et al. |
| 5,738,105 A * | 4/1998 | Kroll .......................... 128/708 |
| 5,741,304 A | 4/1998 | Patwardhan et al. ........... 607/5 |
| 5,749,900 A | 5/1998 | Schroeppel et al. |
| 5,755,736 A | 5/1998 | Gillberg et al. ................. 607/4 |
| 5,755,737 A | 5/1998 | Prieve et al. |
| 5,755,739 A | 5/1998 | Sun et al. |
| 5,759,196 A | 6/1998 | Hess et al. |
| 5,776,072 A * | 7/1998 | Hsu et al. .................... 600/518 |
| 5,778,881 A | 7/1998 | Sun et al. |
| 5,779,645 A | 7/1998 | Olson et al. ................. 600/518 |
| 5,782,888 A | 7/1998 | Sun et al. |
| 5,792,065 A | 8/1998 | Xue et al. |
| 5,795,303 A | 8/1998 | Swanson et al. ............ 600/509 |
| 5,797,399 A | 8/1998 | Morris et al. |
| 5,810,739 A | 9/1998 | Bornzin et al. .............. 600/510 |
| 5,817,133 A | 10/1998 | Houben |
| 5,827,197 A | 10/1998 | Bocek et al. |
| 5,846,263 A | 12/1998 | Peterson et al. |
| 5,855,593 A | 1/1999 | Olson et al. |
| 5,857,977 A | 1/1999 | Caswell et al. |
| 5,868,680 A | 2/1999 | Steiner et al. |
| 5,873,895 A | 2/1999 | Sholder et al. |
| 5,873,897 A | 2/1999 | Armstrong et al. |
| 5,885,221 A * | 3/1999 | Hsu et al. .................... 600/515 |
| 5,893,882 A | 4/1999 | Peterson et al. |
| 5,897,575 A | 4/1999 | Wickham |
| 5,902,324 A | 5/1999 | Thompson et al. |
| 5,935,082 A | 8/1999 | Albrecht et al. |
| 5,941,831 A | 8/1999 | Turcott |
| 5,944,744 A | 8/1999 | Paul et al. |
| 5,951,592 A | 9/1999 | Murphy |
| 5,954,661 A | 9/1999 | Greenspon et al. |
| 5,978,700 A | 11/1999 | Nigam ........................ 600/518 |
| 5,978,707 A | 11/1999 | Krig et al. |
| 5,978,710 A | 11/1999 | Prutchi et al. |
| 5,983,126 A | 11/1999 | Wittkampf ................. 600/509 |

| | | |
|---|---|---|
| 5,983,138 A | 11/1999 | Kramer |
| 5,991,656 A | 11/1999 | Olson et al. |
| 5,991,657 A | 11/1999 | Kim |
| 5,999,850 A | 12/1999 | Dawson et al. |
| 6,024,705 A | 2/2000 | Schlager et al. |
| 6,041,251 A | 3/2000 | Kim et al. |
| 6,049,735 A | 4/2000 | Hartley et al. |
| 6,052,617 A | 4/2000 | Kim |
| 6,052,620 A | 4/2000 | Gillberg et al. |
| 6,076,014 A | 6/2000 | Alt |
| 6,081,745 A | 6/2000 | Mehra |
| RE36,765 E | 7/2000 | Mehra |
| 6,151,524 A | 11/2000 | Krig et al. |
| 6,179,865 B1 * | 1/2001 | Hsu et al. .................. 607/518 |
| 6,181,966 B1 | 1/2001 | Nigam |
| 6,192,273 B1 | 2/2001 | Igel et al. .................. 607/14 |
| 6,212,428 B1 | 4/2001 | Hsu et al. |
| 6,216,032 B1 | 4/2001 | Griffin et al. |
| 6,223,078 B1 | 4/2001 | Marcovecchio |
| 6,224,553 B1 | 5/2001 | Nevo |
| 6,233,487 B1 | 5/2001 | Mika et al. |
| 6,246,909 B1 | 6/2001 | Ekwall |
| 6,253,102 B1 | 6/2001 | Hsu et al. |
| 6,263,242 B1 | 7/2001 | Mika et al. |
| 6,266,554 B1 | 7/2001 | Hsu et al. .................. 600/515 |
| 6,269,263 B1 | 7/2001 | Ohnishi et al. |
| 6,272,377 B1 | 8/2001 | Sweeney et al. |
| 6,275,732 B1 | 8/2001 | Hsu et al. .................. 607/14 |
| 6,301,499 B1 | 10/2001 | Carlson et al. |
| 6,308,095 B1 | 10/2001 | Hsu et al. .................. 600/518 |
| 6,312,388 B1 | 11/2001 | Marcovecchio et al. |
| 6,314,321 B1 | 11/2001 | Morris .................. 607/9 |
| 6,317,632 B1 | 11/2001 | Krig et al. |
| 6,353,759 B1 | 3/2002 | Hartley et al. |
| 6,411,848 B2 | 6/2002 | Kramer et al. |
| 6,430,435 B1 | 8/2002 | Hsu et al. .................. 600/518 |
| 6,430,438 B1 | 8/2002 | Chen et al. |
| 6,434,417 B1 | 8/2002 | Lovett |
| 6,438,410 B2 | 8/2002 | Hsu et al. .................. 600/516 |
| 6,442,425 B1 | 8/2002 | Alt |
| 6,449,503 B1 | 9/2002 | Hsu .................. 600/518 |
| 6,484,055 B1 | 11/2002 | Marcovecchio |
| 6,516,225 B1 | 2/2003 | Florio |
| 6,522,917 B1 | 2/2003 | Hsu et al. .................. 600/518 |
| 6,571,121 B2 | 5/2003 | Schroeppel et al. |
| 6,571,122 B2 | 5/2003 | Schroeppel et al. |
| 6,728,572 B2 | 4/2004 | Hsu et al. |
| 6,889,081 B2 | 5/2005 | Hsu |
| 2002/0072683 A1 | 6/2002 | Schroeppel et al. |
| 2003/0074026 A1 | 4/2003 | Thompson et al. |
| 2003/0109792 A1 | 6/2003 | Hsu et al. |
| 2004/0093035 A1 | 5/2004 | Schwartz et al. |
| 2005/0256544 A1 | 11/2005 | Thompson |

FOREIGN PATENT DOCUMENTS

| | | |
|---|---|---|
| EP | 0469817 A2 | 2/1992 |
| EP | 0506230 A1 | 9/1992 |
| EP | 0540141 | 5/1993 |
| EP | 0879621 | 5/1997 |
| WO | WO-94/06350 A1 | 3/1994 |
| WO | WO-95/09029 A2 | 4/1995 |
| WO | WO-97/11745 A1 | 4/1997 |
| WO | 97/39799 | 10/1997 |
| WO | WO-97/39681 A1 | 10/1997 |
| WO | WO-98/15319 A1 | 4/1998 |
| WO | WO-99/65570 A1 | 12/1999 |
| WO | WO-00/47278 A1 | 8/2000 |
| WO | WO-00/71200 A1 | 11/2000 |
| WO | WO-00/71202 A1 | 11/2000 |
| WO | WO-00/71203 A1 | 11/2000 |
| WO | WO-01/67948 A2 | 9/2001 |

OTHER PUBLICATIONS

LeCarpentier, G.L., et al., "Differentiation of sinus tachycardia from ventricular tachycardia with 1:1 ventriculoatrial conduction in dual chamber implantable cardioverter defibrillators: feasibility of a criterion based on atrioventricular interval.", *PACE 1994*; 17(Pt. I), 1818-1831, (1994).

Thompson, J.A., et al., "Ventriculoatrial conduction metrics for classification of ventricular tachycardia with 1:1 retrograde conduction with dual-chamber sensing implantable cardioverter defibrillators", *J. of Electrocardiography 1998*; 31, 152-156, (1998).

Stadler, Robert W., et al., "An Adaptive Interval-Based Algorithm for Withholding ICD Therapy During Sinus Tachycardia", *PACE*, vol. 26, (2003),1189-1201.

Thompson, Julie , "Template Based AV/VA Interval Comparison for the Discrimination of Cardiac Arrhythmia", U.S. Appl. No. 10/844,475, filed May 12, 2004, 33 pgs.

* cited by examiner

SYSTEM AND METHOD FOR CLASSIFYING TACHYCARDIA ARRHYTHMIAS HAVING 1:1 ATRIAL-TO-VENTRICULAR RHYTHMS

This document is a continuation-in-part of, and claims priority to, U.S. patent application Ser. No. 09/283,159, filed Apr. 1, 1999, now issued as U.S. Pat. No. 6,179,865.

FIELD OF THE INVENTION

The present invention relates generally to implantable medical devices and more particularly to a system and method for classifying 1:1 atrial-to-ventricular cardiac rhythms.

BACKGROUND

The heart is generally divided into four chambers, two atrial chambers and the two ventricular chambers. As the heart beats, the atrial chambers and the ventricular chambers of the heart go through a cardiac cycle. The cardiac cycle consists of one complete sequence of contraction and relaxation of the chambers of the heart. The terms systole and diastole are used to describe the contraction and relaxation phases the chambers of the heart experience during a cardiac cycle. In systole, the ventricular muscle cells are contracting to pump blood through the circulatory system. During diastole, the ventricular muscle cells relax, causing blood from the atrial chambers to fill the ventricular chambers. After the period of diastolic filling, the systolic phase of a new cardiac cycle is initiated.

Control over the timing and order of the atrial and ventricular contractions during the cardiac cycle is critical for the heart to pump blood efficiently. Efficient pumping action of the heart requires precise coordination of the contraction of individual cardiac muscle cells. Contraction of each cell is triggered when an electrical excitatory impulse (an "action potential") sweeps over the heart. Proper coordination of the contractual activity of the individual cardiac muscle cells is achieved primarily by the conduction of the action potential from one cell to the next by gap junctions that connect all cells of the heart into a functional system. In addition, muscle cells in certain areas of the heart are specifically adapted to control the frequency of cardiac excitation, the pathway of conduction and the rate of impulse propagation through various regions of the heart. The major components of this specialized excitation and conduction system include the sinoatrial node (SA node), the atrioventricular node (AV node), the bundle of His, and specialized cells called Purkinje fibers.

The SA node is located at the junction of the superior vena cava and the right atrium. Specialized atrium muscle cells of the SA node spontaneously generate action potentials which are then propagated through the rest of the heart to cause cardiac contraction. This SA node region normally acts as the intrinsic cardiac pacemaker. The action potential generated by the SA node spreads through the atrial wall, causing the atrial chambers to contract and the P-wave of an electrocardiogram signal.

The AV node consists of small, specialized cells located in the lower portion of the atrial chamber. The AV node acts like a bridge for the action potential to cross over into the ventricular chamber of the heart. Once the action potential has crossed over to the ventricular chambers, the bundle of His carries the action potential to specialized cardiac fibers called Purkinje fibers. The Purkinje fibers then distribute the action potential throughout the ventricular chamber of the heart. This results in rapid, very nearly simultaneous excitation of all ventricular muscle cells. The conduction of the action potential through the AV node and into the ventricular chambers creates the QRS-complex of an electrogram signal.

During the cardiac cycle, the action potential moves in an antegrade direction, first causing the atrial chambers to contract and then causing the ventricle chambers to contract. When the action potential causes a single atrial contraction followed by a single ventricular contraction the heart is displaying a one-to-one atrial to ventricular response. In other words, for a given atrial contraction, the cardiac signal causing the atrial contraction subsequently causes a ventricle contraction. In this manner, there is a one-to-one atrial to ventricular response. Cardiac conditions also exist where the action potential moves in a retrograde direction, where the cardiac signal moves from the ventricular chamber up into the atrial chamber.

When a patient's heart rate increases to above 100 beats per minute, the patient is said to be experiencing a tachycardia. Many different types of tachycardias can exist. For example, a heart in a sinus tachycardia (heart rates between 100–180 beats per minute) exhibits a normal cardiac cycle, where action potential moves in the antegrade direction from the atrial chambers to the ventricular chambers to cause the contraction of the heart. The increased heart rate during the sinus tachycardia is a response to a stimulus, and not to a cause within the heart. For example, sinus tachycardia stimulus can include physiologic responses to maintain adequate cardiac output and tissue oxygenation during exercise. Unlike sinus tachycardia, a ventricular tachycardia (heart rates between 120–250) is caused by electrical disturbances within the heart, and not due to the physiological demands of the body. Ventricular tachycardias must be treated quickly in order to prevent the tachycardia from degrading into a life threatening ventricular fibrillation.

Distinguishing a ventricular tachycardia from a sinus tachycardia is important for diagnosing and properly treating the patient's cardiac condition. Misdiagnosis of a sinus tachycardia as a ventricular tachycardia can lead to inappropriate treatment. Difficulty in distinguishing among tachyarrhythmias increases when the heart is displaying a one-to-one atrial to ventricular rhythm. One reason for this difficulty is that the action potentials generated during the tachyarrhythmia can travel either in the antegrade direction, from the atria to the ventricles, or in a retrograde direction, from the ventricles into the atria. Tachyarrhythmias having action potentials conducted in an antegrade direction include sinus tachycardia and atrial tachycardia. Tachyarrhythmias having action potentials conducted in a retrograde direction include ventricular tachycardia with 1-to-1 retrograde conduction. Distinguishing the direction of the action potential (antegrade or retrograde) during a tachyarrhythmia is important in diagnosing and delivering the appropriate type of treatment to the patient.

Ways of classifying one-to-one tachyarrhythmias have been suggested. For example, Thompson et al. (*J. Of Electrocardiography* 1998; 31:152–156) have suggested that VA intervals can be compared to a retrograde zone, where the retrograde zone is defined as a zone between a predetermined upper time bound and a lower time bound relative the ventricular contractions. A rhythm whose VA intervals fall inside the retrograde zone is classified as retrograde. Otherwise, the rhythm is classified as an antegrade rhythm. However, limitations to this suggested method exist. For example, the VA intervals can change with the heart rate. Also, patients with first degree heart block (PR>200 milliseconds) may have short VA during sinus tachycardia or normal sinus rhythm. Thus, a need exists in the art for a reliable and convenient approach which can distinguish antegrade and retrograde action potentials during a one-to-one tachyarrhythmia episode.

SUMMARY OF THE INVENTION

The present subject matter provides a system and a method for distinguishing antegrade from retrograde action potentials during a 1:1 atrial-to-ventricular tachyarrhythmia episode. The classified action potentials are then used to classify the tachyarrhythmia episode as occurring in either a retrograde direction or an antegrade direction. Based on this classification it is then possible to determine an appropriate course of treatment.

Discriminating one-to-one atrial-to-ventricular rhythms conducted in an antegrade direction (e.g., sinus tachycardia, atrial tachycardia) from one-to-one rhythms conducted in a retrograde direction (e.g., VT with one-to-one retrograde conduction) is an important aspect of properly diagnosing a tachyarrhythmia episode. The present subject matter utilizes two or more sensed cardiac signals, where at least a first cardiac signal is sensed from the ventricular region of the heart and at least a second cardiac signal is sensed from a supraventricular region of the heart. Each cardiac signal includes indications of cardiac complexes, where the cardiac complexes are the electrical excitatory impulses, or action potentials, sensed as the heart goes through the cardiac cycle. Information derived from the cardiac complexes in the two or more cardiac signals is then used in classifying, or distinguishing, the conduction direction (e.g., antegrade or retrograde) of the cardiac action potential.

In one embodiment, a first cardiac signal and a second cardiac signal are sensed. In one embodiment, the first cardiac signal is sensed from a ventricular location and the second cardiac signal is sensed from a supraventricular location. Ventricular depolarizations are sensed, or detected, from the first cardiac signal and atrial depolarizations are sensed, or detected, from the second cardiac signal. The first and second cardiac signals are analyzed to detect the occurrence of a tachycardia episode having a one-to-one association of atrial depolarizations to ventricular depolarizations. In one embodiment, the association of atrial depolarizations to ventricular depolarizations are analyzed to determine if a one-to-one association of atrial depolarizations to ventricular depolarizations exists during the tachycardia episode.

Once a tachycardia episode having a one-to-one association of atrial depolarizations to ventricular depolarizations is detected, time intervals are measured between predetermined features on combinations of the first cardiac signal and the second cardiac signal. In one embodiment, first intervals are measured between ventricular depolarizations detected in the first cardiac signal and first predetermined cardiac events in either the first or second cardiac signal. Similarly, second intervals are measured between atrial depolarizations detected in the second cardiac signal and second predetermined cardiac events in either the first or second cardiac signal.

The values of the first intervals are then used to calculate, or determine, a first interval characteristic, or dispersion, of intervals from the first intervals and the second intervals are used to calculate, or determine, a second interval characteristic, or dispersion, of intervals from the second intervals. The values for the first interval characteristic and the second interval characteristic are then used to classify the tachycardia episode as either occurring in an antegrade direction or in a retrograde direction. In one embodiment, the first interval characteristic and the second interval characteristic are compared in classifying the tachycardia episode based on the first interval characteristic and the second interval characteristic.

In one embodiment, the first interval characteristic and the second interval characteristic are a first variance value and a second variance value, respectively. However, other first interval and second interval characteristics exist and can be used with the present subject matter. For example, the first interval and second interval characteristics can include calculating and using a first range and a second range of values which are then compared is classifying a tachycardia episode as either occurring in an antegrade or retrograde direction.

In one embodiment, a first predetermined series of the first intervals and a second predetermined series of the second intervals are used to calculate the first interval and the second interval characteristics, respectively. The values of the first interval and the second interval characteristics are then compared. In one embodiment, the comparison between the two characteristic values is between a first variance value and a second variance value, where the comparison is to determine which value is larger. Based on the comparison, the tachycardia episode is then classified as either occurring in an antegrade direction or is a retrograde direction. In one embodiment, the tachycardia episode is classified as an antegrade rhythm, or occurring in the antegrade direction, when the value of the second variance is less than or equal to the value of the first variance. Alternatively, the tachycardia episode is classified as an retrograde rhythm, or occurring in the retrograde direction, when the value of the second variance is greater than the value of the first variance.

DETAILED DESCRIPTION

Figure 1:
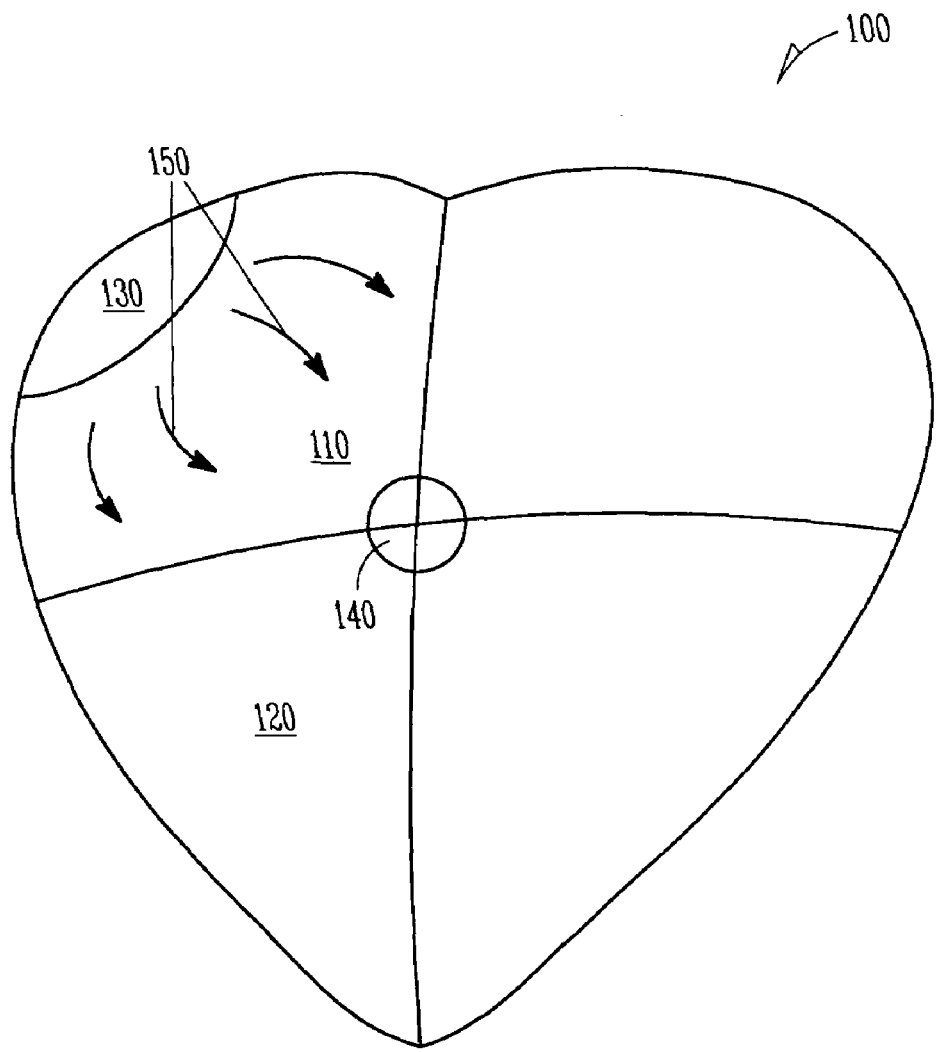
FIG. 1 is a schematic of a heart.

In the following detailed description, reference is made to the accompanying drawings which form a part hereof and in which is shown by way of illustration specific embodiments in which the invention can be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

The embodiments illustrated herein are demonstrated in an implantable cardiac defibrillator (ICD), which may include numerous defibrillation, pacing, and pulse generating modes known in the art. However, these embodiments are illustrative of some of the applications of the present system, and are not intended in an exhaustive or exclusive sense. The concepts described herein can be used in a variety of applications which will be readily appreciated by those skilled in the art upon reading and understanding this description. For example, the present system is suitable for implementation in a variety of implantable, such as an implantable pacemaker, and external medical devices.

As discussed above, discriminating one-to-one atrial-to-ventricular rhythms conducted in an antegrade direction (e.g., sinus tachycardia, atrial tachycardia) from one-to-one rhythms conducted in a retrograde direction (e.g., VT with one-to-one retrograde conduction) is an important aspect of properly diagnosing a tachyarrhythmia episode. The present subject matter utilizes two or more sensed cardiac signals, where at least a first cardiac signal is sensed from the ventricular region of the heart and at least a second cardiac signal is sensed from a supraventricular region of the heart. Each cardiac signal includes indications of cardiac complexes, where the cardiac complexes are the electrical excitatory impulses, or action potentials, sensed as the heart goes through the cardiac cycle. Information derived from the cardiac complexes in the two or more cardiac signals is then used in classifying, or distinguishing, the conduction direction of the cardiac action potential.

The present subject matter discriminates and classifies tachyarrhythmias displaying a one-to-one atrial to ventricular rhythm as either being conducted in an antegrade direction or in a retrograde direction. In one embodiment, intervals between predetermined points on an atrial cardiac signal and/or a ventricular cardiac signal are used in determining whether the tachyarrhythmia is being conducted in the antegrade or retrograde direction. In one embodiment, this determination is based on the variability between alike measurements on the atrial cardiac signal and/or the ventricular cardiac signal. The variability from measurements taken from the atrial cardiac signal and/or the ventricular cardiac signal is then used to classify the tachyarrhythmia as either occurring in the antegrade or the retrograde direction.

The present subject matter has a distinct advantage over previously described systems and methods for classifying one-to-one atrial-to-ventricular in that the cardiac complex detected during a tachycardia episode need not be compared to a "template" or a predetermined cardiac complex in order to classify the cardiac complex as occurring in either the antegrade or retrograde direction. Previous approaches have relied upon a "template" cardiac complex (i.e., an idealized cardiac complex) which was stored in the memory of the implantable device. Upon detecting a tachycardia episode, the system would retrieve the "template" cardiac complex and then proceed to compare the template cardiac complex to the cardiac complexes sensed during the tachycardia episode. This process takes time and energy, two factors which are reduced by the present subject matter as the need for a "template" cardiac complex has been eliminated. In place of a template cardiac complex the present subject matter utilizes characteristics of the intervals measured between predetermined features on cardiac complexes sensed in at least a first cardiac signal and a second cardiac signal during the tachycardia episode. No predetermined template or cardiac signals are required, thus saving both computational time and electrical energy.

Referring now to FIG. 1, there is shown a drawing of a human heart 100. The heart 100 is divided into atrial chambers 110 and ventricular chambers 120. When the heart 100 is in normal sinus rhythm or in sinus tachycardia the depolarization wave (action potential) for the heart beat originates in the SA node 130, which is located in the atrial region of the heart 100. In this situation the atrial chambers 110 can be thought of as originating the signals to start the contraction of the heart 100. The depolarization wave moves from the SA node 130 across the atria and then to the AV node 140. Lines 150 show the direction of the depolarization wave as it would move across the atrial chambers 110. The AV node consists of small specialized cells located on the right side of the atrial septum just under the endocardium. The lower portion of the AV node consists of parallel fibers that form a "bridge" of contiguous cardiac cells crossing the cartilaginous structure that provides support for the cardiac valves and electrically separates atria from ventricles. Propagation of the impulse through this AV nodal region is typically very slow (approximately 0.05 m/s) and therefore a delay is imposed between excitation of the atria and the ventricles. The term AV delay is given to denote this delay. The action potential causing the depolarization wave then moves through the AV node and down into the ventricle chambers 120. The depolarization wave is distributed quickly and essentially evenly through out the ventricle chambers 120 which allows for near simultaneous contraction of ventricles of the heart 100.

When the depolarization wave originates in the SA node and moves through the AV node into the ventricles, the depolarization wave is said to be moving in an antegrade direction. Examples of when the depolarization wave is moving in the antegrade direction include when the heart is in normal sinus rhythm or when the heart is in sinus tachycardia. There are also cardiac conditions in which the depolarization wave, or action potential, can move in a retrograde direction. In this situation the cardiac signal moves from the ventricular chamber up into the atrial chamber. An example of a cardiac condition displaying a retrograde direction is ventricular tachycardia with 1-to-1 retrograde conduction. During a tachycardia episode, having a fast and reliable method and system for discriminating one-to-one atrial-to-ventricular rhythms conducted in an antegrade direction (e.g., sinus tachycardia, atrial tachycardia) from one-to-one rhythms conducted in a retrograde direction (e.g., VT with one-to-one retrograde conduction) is important for quickly and accurately diagnosing the tachyarrhythmia episode.

Figure 2:
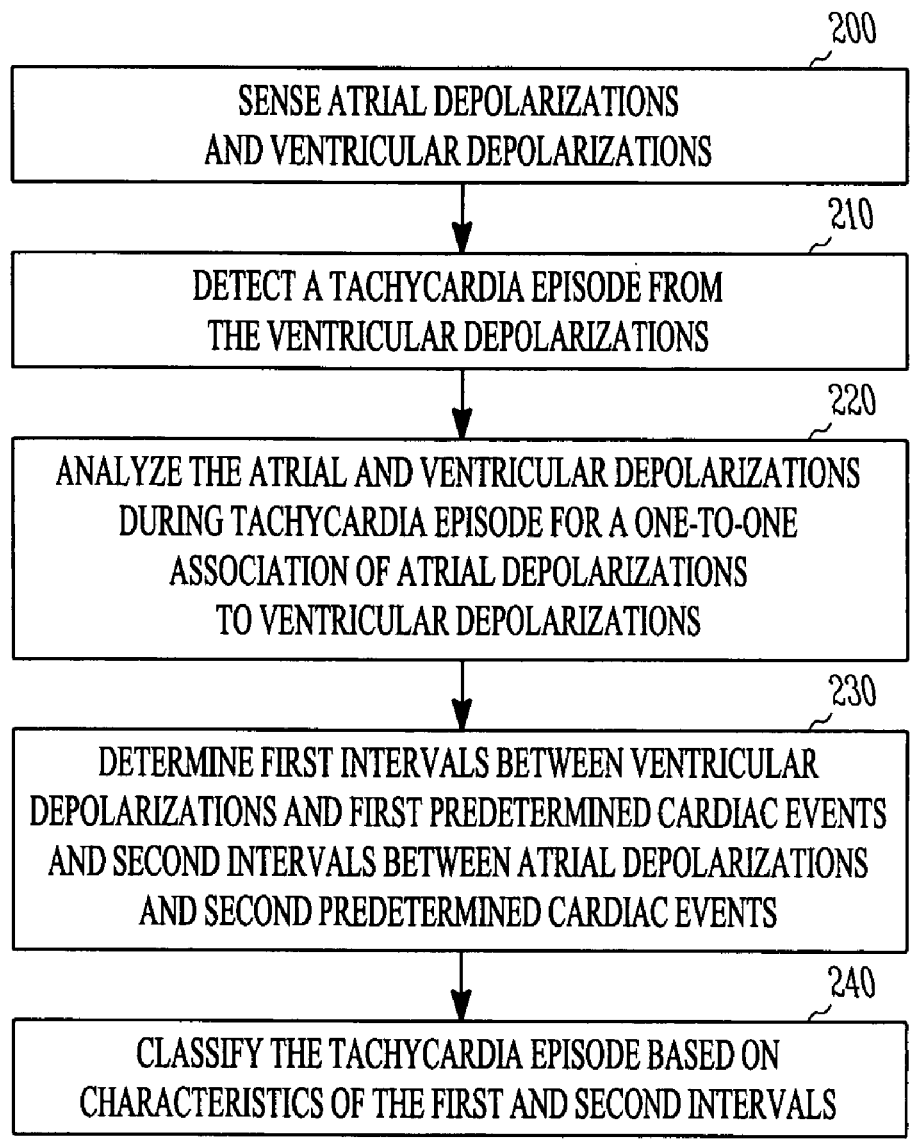
FIG. 2 is a flow chart illustrating one embodiment of the present subject matter.

Referring now to FIG. 2, there is shown one embodiment of a method for the present subject matter. At 200, ventricular depolarizations and atrial depolarizations are sensed. In one embodiment, the ventricular depolarizations are sensed, or detected, in a first cardiac signal and the atrial depolarizations are sensed, or detected, in a second cardiac signal. In one embodiment, the first cardiac signal is sensed from a ventricular location and the second cardiac signal is sensed from an supraventricular location. For example, the first cardiac signal is sensed across a ventricular region which includes at least a right ventricular chamber and the second cardiac signal is sensed across a right atrial chamber location. Alternatively, the second cardiac signal is sensed from a location within the coronary sinus vein or other coronary vein which would allow for the cardiac signal to be sensed from the supraventricular region of the heart. Additionally, the first and second cardiac signals are any combination of rate (near field) and/or morphology (far field) signals. In one embodiment, the first cardiac signal sensed from the ventricular region is a morphology signal and the second cardiac signal sensed from the supraventricular location is a rate signal.

At 210, ventricular depolarizations are analyzed to detect the occurrence of a tachycardia episode. In one embodiment, the occurrence of a tachycardia episode is determined from time intervals between the sensed ventricular intervals. The atrial and ventricular depolarizations are then analyzed during a detected tachycardia episode to determine if there is a one-to-one association of atrial depolarizations to ventricular depolarizations at 220. In the present subject matter, the occurrence of a tachycardia episode is defined generally as a heart rate in the range of 120–250 beats per minute which results from electrical disturbances within the heart, and not due to the physiological demands of the body. In one embodiment, the heart rate is determined from the ventricular depolarizations detected in the first cardiac signal.

Once a tachycardia episode having a one-to-one association of atrial depolarizations to ventricular depolarizations is detected, time intervals are measured between predetermined features on combinations of the atrial depolarizations and the ventricular depolarizations. For example, during the tachycardia episode that has the one-to-one association of atrial depolarizations to ventricular depolarizations, first intervals are measured between the ventricular depolarizations and first predetermined cardiac events and second intervals are measured between the atrial depolarizations and second predetermined cardiac events at 230.

In one embodiment, values of the first and second intervals are analyzed to determine whether the value of a given interval falls outside of a predetermined threshold value. In one embodiment, interval values falling outside the predetermined threshold (e.g., intervals longer than the threshold and/or intervals shorter than the threshold) are not utilized in the present subject matter. In one embodiment, the predetermined threshold is a percentage, or ratio, of a predetermined number of the most current interval values. Alternatively, the morphology (i.e., shape) and/or direction (i.e., trajectory) of the sensed depolarization are used to determine whether the sensed wave is used in determining time intervals.

Figure 3:
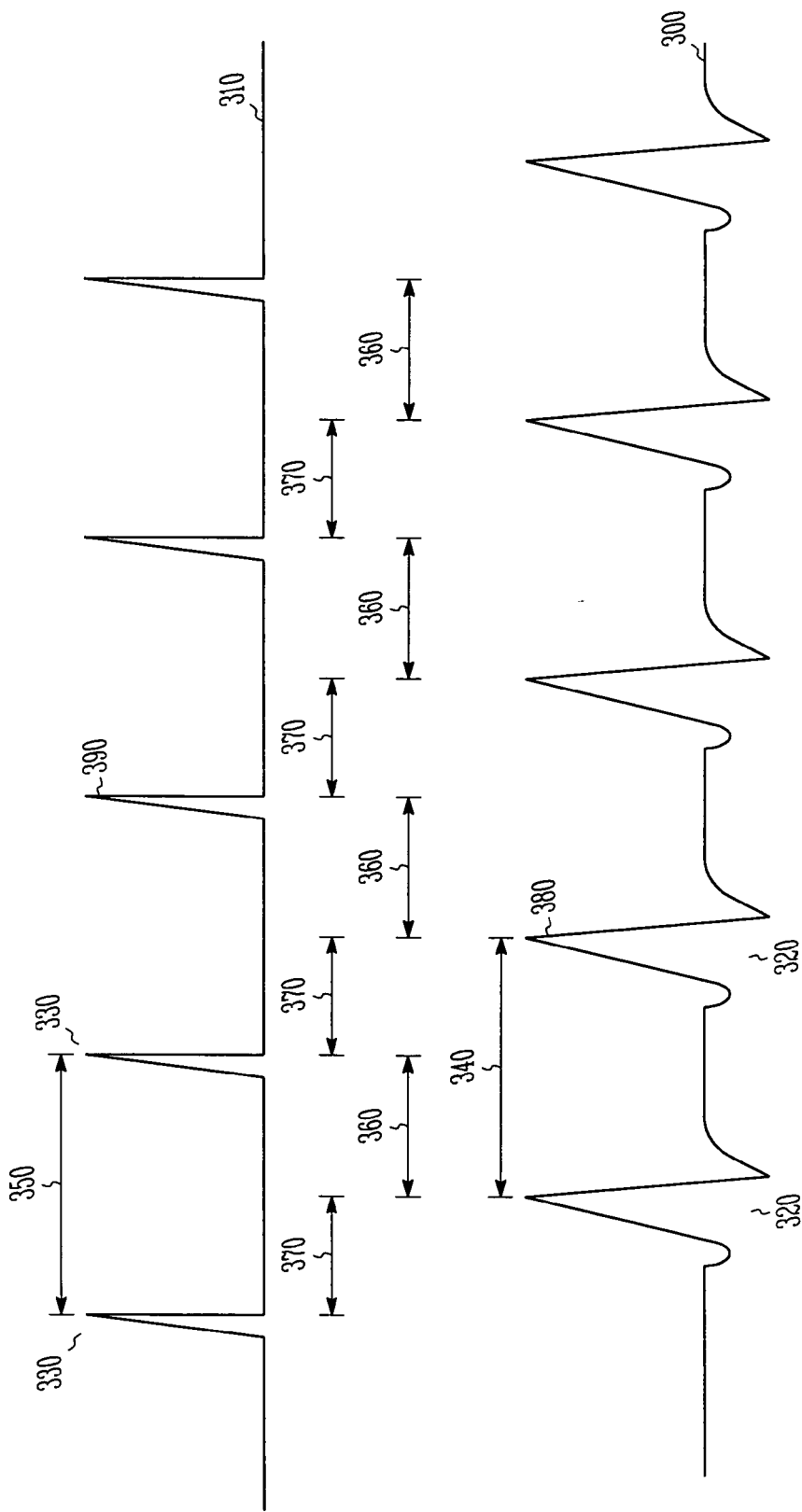
FIG. 3 is a schematic illustrating one embodiment of a first cardiac signal and a second cardiac signal.

Referring now to FIG. 3, there are shown examples of various combinations of signal features used when measuring, or calculating, the first and second intervals. FIG. 3 displays one embodiment of a first cardiac signal 300 and a second cardiac signal 310 being used in the present subject matter. The first cardiac signal 300 is sensed from a ventricular region of the heart and the second cardiac signal 310 is sensed from an atrial region of the heart. The first cardiac signal 300 includes indications of ventricular depolarizations which are sensed in any number of ways, including use of implanted intravascular leads having one or more electrodes for sensing a rate signal (near field signal) and/or a morphology signal (far field signal) in either unipolar or bipolar sensing mode. In one embodiment, the sensed ventricular depolarizations are the R-waves of a sensed electrocardiogram signal. Alternatively, the sensed ventricular depolarizations include QRS-complexes detected in the first cardiac signal. In the present embodiment, the sensed ventricular depolarizations in the first cardiac signal 300 are QRS-complexes which are shown generally at 320.

The second cardiac signal 310 includes indications of atrial depolarizations which are sensed in any number of ways, including use of implanted intravascular leads having one or more electrodes for sensing a rate signal (near field signal) and/or a morphology signal (far field signal) in either unipolar or bipolar sensing mode. In one embodiment, the sensed atrial depolarizations are the P-waves of a sensed electrocardiogram signal. In the present embodiment, the sensed atrial depolarizations in the second cardiac signal 310 are P-waves which are shown generally at 330.

The embodiment of the first and second cardiac signal shown in FIG. 3 is an example of a one-to-one atrial-to-ventricular rhythm. As FIG. 3 shows, for each sensed atrial depolarization 330 there is a subsequent ventricular depolarization 320 which occurs before the next atrial depolarization. As previously discussed, time intervals are measured between at least two different combinations of atrial and ventricular depolarizations. For example, first intervals are measured and calculated between pairs of detected ventricular depolarizations 320 and first predetermined cardiac events. Similarly, the second intervals are measured and calculated between pairs of detected atrial depolarizations 330 and second predetermined cardiac events.

In one embodiment, the first predetermined cardiac events are ventricular depolarizations 320 detected in the first cardiac signal 300 and the second predetermined cardiac events are atrial depolarizations 330 detected in the second cardiac signal 310. Thus, the first intervals are measured between a ventricular depolarization 320 and a subsequent ventricular depolarization. This measurement is a ventricular—ventricular (VV)-interval measurement (also known as a ventricular cycle length) which is the time between successively sensed ventricular depolarizations. An example of the VV-interval measurement is shown at 340. As for the second intervals, they are measured between an atrial depolarization 330 and a subsequent atrial depolarization. This measurement is an atrial—atrial (AA)-interval measurement (also known as atrial cycle lengths) which is the time between successively sensed atrial depolarizations. An example of the AA-interval measurement is shown at 350.

In an alternative embodiment, the first predetermined cardiac events are atrial depolarizations 330 detected in the second cardiac signal 310 and the second predetermined cardiac events are ventricular depolarizations 320 detected in the first cardiac signal 300. Thus, the first intervals are measured between a ventricular depolarization 320 and a subsequent atrial depolarization. These measurements are ventricular-atrial (VA)-interval measurements of the time between a ventricular depolarization 320 and a subsequent atrial depolarization 330. An example of the VA-interval measurement is shown at 360. The second intervals are measured between an atrial depolarization 330 and a subsequent ventricular depolarization. These measurements are atrial-ventricular (AV)-interval measurement of the time between an atrial depolarization 330 and a subsequent ventricular depolarization 320. An example of the AV-interval measurement is shown at 370.

In one embodiment, interval measurements made on the first cardiac signal and the second cardiac signal take place between predetermined points on the sensed cardiac complexes. In one embodiment, the predetermined points are repeatably identifiable portions of the cardiac complex in the cardiac signal. In one embodiment, the predetermined points are selected by a physician and are subsequently programmed into the medical device system (e.g., an ICD) for use with the present subject matter. Examples of repeatably identifiable portions of cardiac complexes include the maximum (or minimum) deflection point of the cardiac signal during the cardiac complex, the point of maximum slope of the cardiac signal during the cardiac complex, or the start or end of a cardiac complex detected in the cardiac signal. Other repeatably identifiable portion of cardiac complexes could also be used.

Examples of predetermined points are shown in FIG. 3. FIG. 3 shows an example of a first predetermined point 380 located along the ventricular depolarizations. In the present embodiment, the first predetermined point 380 is a maximum deflection point of the first cardiac signal. Also shown in FIG. 3 is an example of a second predetermined point 390 located along the atrial depolarizations. In the present embodiment, the second predetermined point 390 is a maximum deflection point of the second cardiac signal.

In one embodiment, the values of a plurality of first intervals and the values of a plurality of second intervals are used to determine, or calculate, characteristics of the first and second intervals (e.g., first characteristics and second characteristics). At 240, the characteristics of the first and second intervals are then used to classify the tachycardia episode as either an antegrade rhythm or a retrograde rhythm based on characteristics of the first and second intervals. In one embodiment, the characteristics of the first and second intervals include first interval characteristics and second interval characteristics, where the values for the first interval characteristics and second interval characteristics are calculated from the first and second intervals. The tachycardia episode is then classified based on the first interval characteristic and the second interval characteristic. In one embodiment, characteristic means some metric of the interval set that quantifies its variability. For example, the first interval characteristic can be a first variance value, $\sigma^2(x)$, calculated from the first intervals, and the second interval characteristic can be a second variance value, $\sigma^2(y)$, calculated from the second intervals. In one embodiment, the tachycardia episode is then classified based on the first variance value and the second variance value.

In addition to variance (i.e., the second moment of the intervals), other examples of first characteristics and second characteristics that can be used to describe the variability of the first intervals and the second intervals respectively include, but are not limited to, other moments of the intervals, the size of the maximal range (i.e., the maximum interval size–minimum interval size), a percentile range (i.e., the size of the range that is centered on the average interval size and which includes a specified percentage of the intervals–such as range that includes the center 50% of the intervals), or a range that is based on the first (second, third, etc.) smallest intervals to the first (second, third, etc.) largest intervals. Alternate embodiments use these alternate first and second characteristics to classify the tachycardia episodes.

In one embodiment, a first predetermined series of the first intervals and a second predetermined series of the second intervals are used to calculate the first interval characteristic and the second interval characteristic, respectively. In one embodiment, the first and second predetermined series of intervals are programmable and have a value of at least five (5) intervals. In an alternative embodiment, the first and second predetermined series are programmable values in the range of between five (5) and fifty (50), five (5) and twenty five (25), ten (ten) and fifty (50), or ten (10) and twenty five (25), where ten is an acceptable value.

Figure 4:
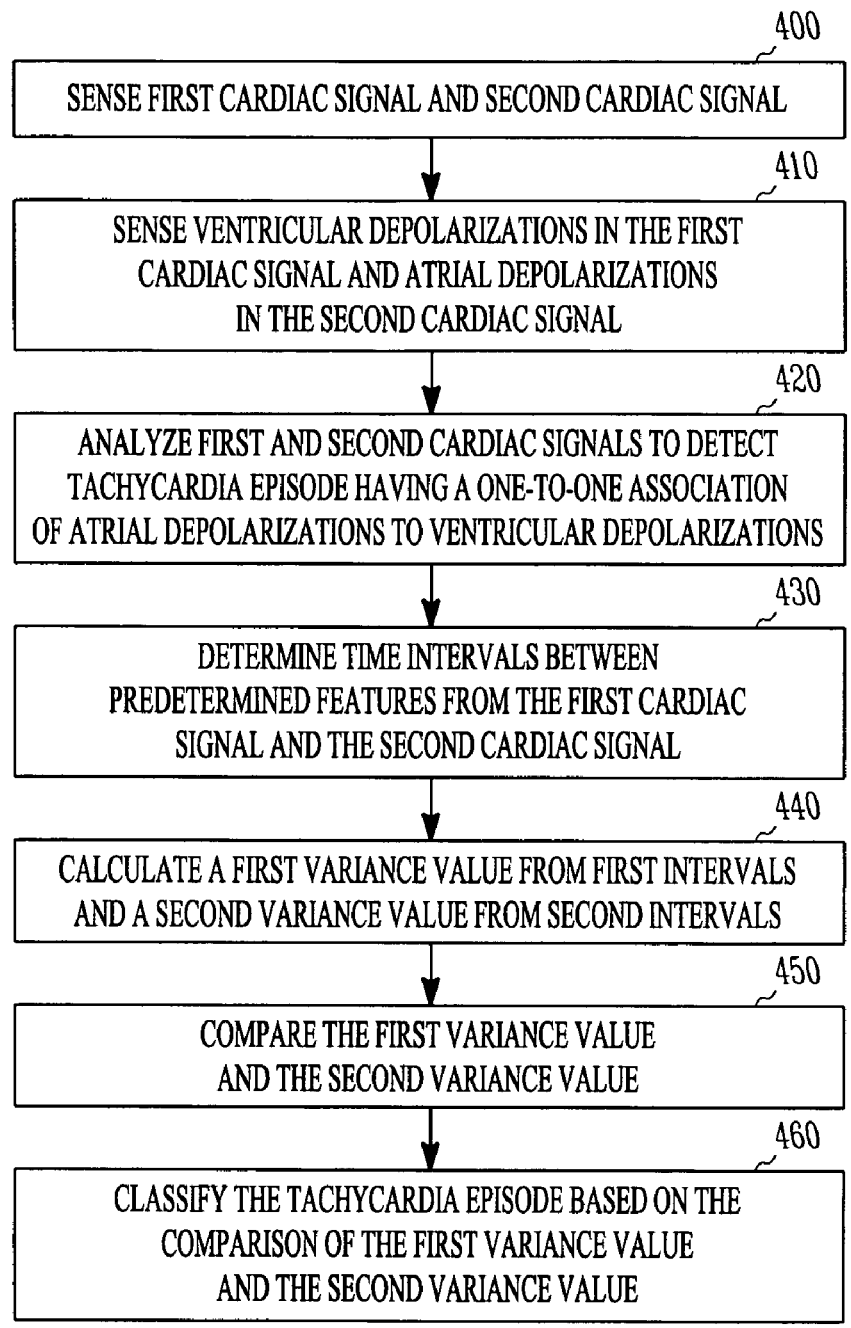
FIG. 4 is a flow chart illustrating one embodiment of the present subject matter.

Referring now to FIG. 4, there is shown one embodiment of a method for the present subject matter. At 400, a first cardiac signal and a second cardiac signal are sensed. In one embodiment, the first cardiac signal is sensed from a ventricular location and the second cardiac signal is sensed from an supraventricular location. For example, the first cardiac signal is sensed across a ventricular region which includes at least a right ventricular chamber and the second cardiac signal is sensed across a right atrial chamber location. Alternatively, the second cardiac signal is sensed from a location within the coronary sinus vein or other coronary vein which would allow for the cardiac signal to be sensed from the supraventricular region of the heart. Additionally, the first and second cardiac signals are any combination of rate (near field) and/or morphology (far field) signals. In one embodiment, the first cardiac signal sensed from the ventricular region is a morphology signal and the second cardiac signal sensed from the supraventricular location is a rate signal.

At 410, ventricular depolarizations are sensed, or detected, from the first cardiac signal and atrial depolarizations are sensed, or detected, from the second cardiac signal. The first and second cardiac signals are analyzed to detect the occurrence of a tachycardia episode having a one-to-one association of atrial depolarizations to ventricular depolarizations at 420. In one embodiment, the association of atrial depolarizations to ventricular depolarizations are analyzed to determine if a one-to-one association of atrial depolarizations to ventricular depolarizations exists during the tachycardia episode. In the present subject matter, the occurrence of a tachycardia episode is defined generally as a heart rate in the range of 120–250 beats per minute which results from electrical disturbances within the heart, and not due to the physiological demands of the body. In one embodiment, the heart rate is determined from the ventricular depolarizations detected in the first cardiac signal.

Once a tachycardia episode having a one-to-one association of atrial depolarizations to ventricular depolarizations is detected, time intervals are measured between predetermined features on combinations of the first cardiac signal and the second cardiac signal at 430. In one embodiment, first intervals are measured between ventricular depolarizations detected in the first cardiac signal and first predetermined cardiac events in either the first or second cardiac signal. Similarly, second intervals are measured between atrial depolarizations detected in the second cardiac signal and second predetermined cardiac events in either the first or second cardiac signal. In one embodiment, values of the first and second intervals are analyzed to determine whether the value of a given interval falls outside of a predetermined threshold value. In one embodiment, interval values falling outside the predetermined threshold (e.g., intervals longer than the threshold and/or intervals shorter than the threshold). In one embodiment, the predetermined threshold is a percentage, or ratio, of a predetermined number of the most current interval values. Alternatively, the morphology (i.e., shape) and/or direction (i.e., trajectory) of the sensed depolarization are used to determine whether the sensed wave is used in determining time intervals.

At 440 the values of a plurality of first intervals are used to determine, or calculate, a first variance value, $\sigma^2(x)$, from the first intervals and the values of a plurality of second intervals are used to determine, or calculate, a second variance value, $\sigma^2(y)$, from the second intervals. In one embodiment, a first predetermined series of the first intervals and a second predetermined series of the second intervals are used to calculate the first variance and the second variance, respectively. In one embodiment, the first and second predetermined series of intervals are programmable and have a value of at least five (5) intervals. In an alternative embodiment, the first and second predetermined series are programmable values in the range of between five (5) and fifty (50), five (5) and twenty five (25), ten (ten) and fifty (50), or ten (10) and twenty five (25), where ten is an acceptable value.

The values of the first variance and the second variance are then compared at 450. In one embodiment, the comparison between the two variance values is to determine which variance value is larger. Based on the comparison of the first variance value and the second variance value, the tachycardia episode is then classified as either occurring in an antegrade direction or is a retrograde direction at 460. In one embodiment, the tachycardia episode is classified as an antegrade rhythm, or occurring in the antegrade direction, when the value of the second variance is less than or equal to the value of the first variance. Alternatively, the tachycardia episode is classified as an retrograde rhythm, or occurring in the retrograde direction, when the value of the second variance is greater than the value of the first variance.

Figure 5A:
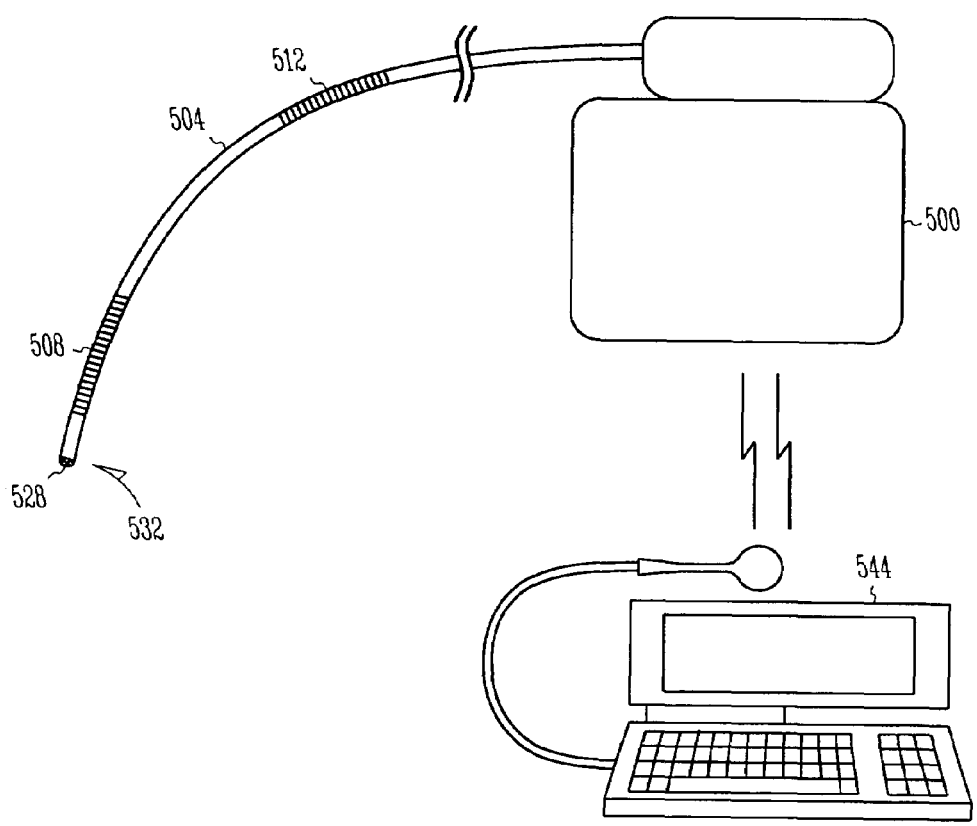
FIG. 5A is a schematic view of one embodiment of an implantable medical device according to one embodiment of the present subject matter.

Referring now to FIG. 5A, there is shown one embodiment of a system according to the present subject matter. The system includes an implantable cardiac defibrillator 500 and at least one cardiac lead including at least three electrodes. In one embodiment, the at least one cardiac lead is a ventricular lead 504. The ventricular lead 504 includes at least a first electrode 508 and a second electrode 512. FIG. 5A shows an embodiment in which the first electrode 508 is a defibrillation coil electrode positioned along a peripheral surface of the ventricular lead 504. The first electrode 508 is connected to the electronic circuitry within the implantable cardiac defibrillator 500 through a lead conductor housed and electrically insulated within the body of the ventricular lead 504. The second electrode 512 is also a defibrillation coil electrode which is positioned along the peripheral surface of the ventricular lead 504. The second electrode 512 is located at a position that is proximal to the first electrode 508 which allows for the ventricular lead 504 to be implanted within the vasculature with the first electrode 508 positioned in the right ventricle and the second electrode 512 positioned in either the right atrial chamber or a major vein leading to the right atrial chamber of the heart. In one embodiment, the first and second electrodes, 508 and 512, are used to sense, or detect, a cardiac morphology signal from the heart. In one embodiment, the cardiac morphology signal sensed from the heart includes both atrial and ventricular signals. In an additional embodiment, the electrically conductive portion of the implantable cardiac defibrillator 500 housing is used in conjunction with the first and second electrodes 508, 512 to allow for a morphology signal to be sensed between three electrodes.

In addition to the first and second electrodes 508, 512, the ventricular lead 504 is shown further including a pacing electrode 528 located at or adjacent a distal end 532 of the ventricular lead 504. This allows for both rate and morphology signals to be sensed from the ventricular region of the heart using the supplied electrodes, where, for example, the rate signal is sensed between the pacing electrode 528 and the first electrode 508 and the morphology signal is sensed between the first and second electrodes 508, 512.

Figure 5B:
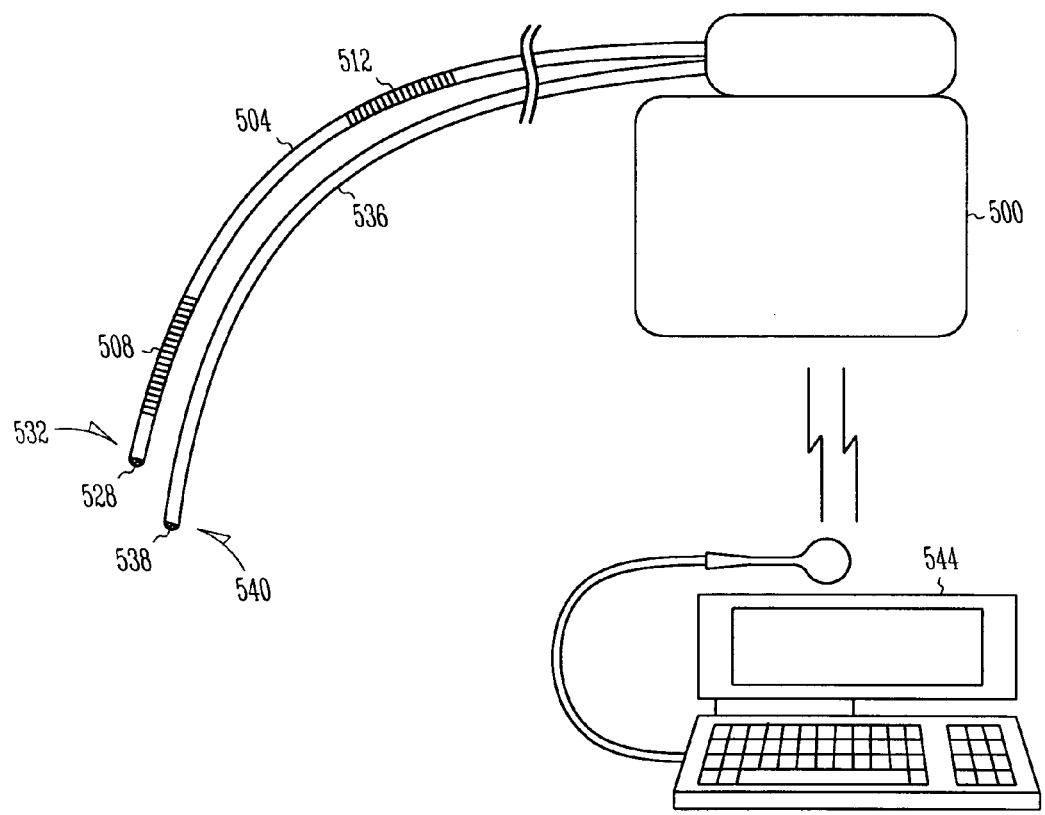
FIG. 5B is a schematic view of one embodiment of an implantable medical device according to one embodiment of the present subject matter.

Referring now to FIG. 5B, there is shown an additional embodiment of the system according to the present subject matter. The system includes the implantable cardiac defibrillator 500, the ventricular lead 504 and an atrial lead 536. The atrial lead 536 includes a first atrial electrode 538, which in FIG. 5B is shown positioned at a distal end 540 of the atrial lead 536. The first atrial electrode 538 is connected to electronic circuitry within the implantable cardiac defibrillator 500 through a lead conductor housed and electrically insulated within the body of the atrial lead 536. The lead conductor allows for cardiac signals sensed using the first atrial electrode 538 to be supplied to the electronic circuitry and for pacing pulses generated though the use of the electronic circuitry to be delivered to the first atrial electrode 538. In the present embodiment, unipolar sensing and pacing is accomplished between the first atrial electrode 538 and an electrically conductive portion of the implantable cardiac defibrillator 500 housing.

In one embodiment, the atrial lead 536 and the ventricular lead 504 have elongated bodies made of one or more materials suitable for implantation in a human body, where such materials are known in the art. Additionally, the first and second electrodes 508, 512, the pacing electrode 528 and the first atrial electrode 538 are constructed of electrically conductive materials, such as platinum, platinum-iridium alloys, or other alloys as are known. The lead conductors are also constructed of electrically conductive materials such as MP35N, an alloy of nickel, chromium, cobalt, and molybdenum.

FIG. 5 also shows a medical device programmer 544. The medical device programmer 544 and the implantable cardiac defibrillator 500 include communication circuitry which allows for cardiac data to be to and from the implantable cardiac defibrillator 500. In addition, command signals for controlling the operation of the implantable cardiac defibrillator 500 can also be sent between the medical device programmer 544 and the implantable cardiac defibrillator 500. In one embodiment, communication between the medical device programmer 544 and the implantable cardiac defibrillator 500 is established over a radio frequency telemetry channel as is known in the art.

Figure 6:
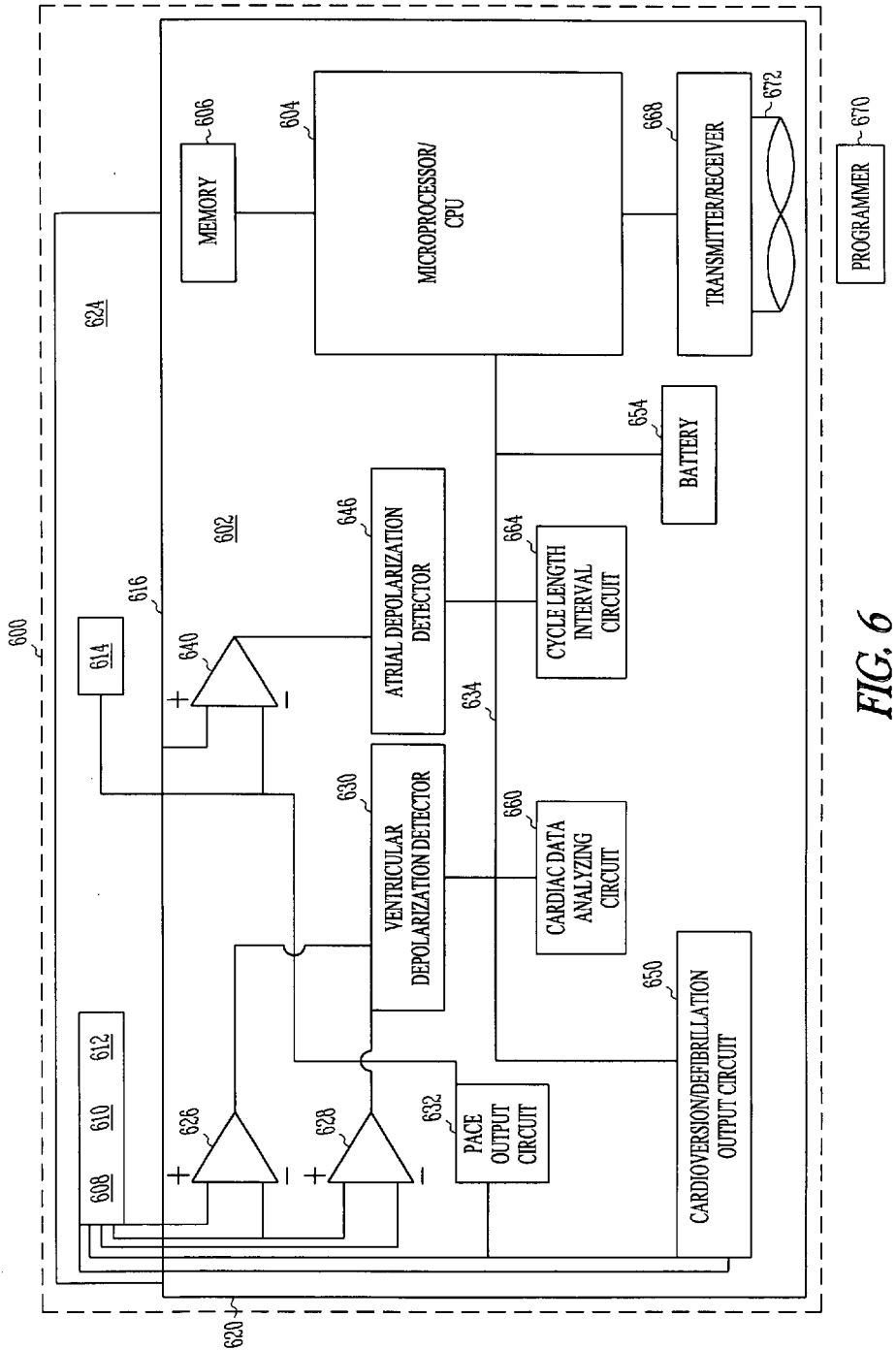
FIG. 6 is a block diagram of one embodiment of an implantable medical device according to the present subject matter.

Referring now to FIG. 6, there is shown a block diagram of an implantable cardiac defibrillator (ICD) 600 according to one embodiment of the present subject matter. The ICD 600 includes control circuitry 602 which receives one or more cardiac signals and delivers electrical energy to electrodes positioned on the atrial and ventricular leads under predetermined conditions.

In one embodiment, the control circuitry 602 is a programmable microprocessor-based system, with a microprocessor 604 and a memory circuit 606, which contains parameters for various pacing and sensing modes and stores data indicative of cardiac signals received by the control circuitry 602. The control circuitry 602 includes terminals labeled with reference numbers 608, 610, 612, 614 and 616 for connection to the electrodes attached to the surface of a ventricular lead and an atrial lead. In the embodiment shown in FIG. 5B, the first electrode 508 is coupled to terminal 608 through a first electrically insulated conductor provided within the ventricular lead 504. The second electrode 512 is coupled to terminal 610 through a second electrically insulated conductor provided within the ventricular lead 504. The pacing electrode 528 on the ventricular lead 504 is coupled to terminal 612 through a third electrically insulated conductor provided within the ventricular lead 504. Finally, the first atrial electrode 538 is coupled to terminals 614 by electrically insulated conductors provided within the atrial lead 536.

The control circuitry 602 is encased and hermetically sealed in a housing 620 suitable for implanting in a human body. In one embodiment, the housing 620 is made of titanium, however, other biocompatible housing materials as are known in the art may be used. A connector block 624 is additionally attached to the housing 620 to allow for the physical and the electrical attachment of the ventricular lead 504, the atrial lead 536 and the electrodes to the ICD 600 and the encased control circuitry 602.

Sense amplifiers 626 and 628 are coupled to the control circuitry 602, and are electrically coupled to terminals 608, 610 and 612 to allow for a first cardiac signal to be sensed between the ventricular electrode 528 and first defibrillation electrode 508 and/or between the first electrode 508 and the second electrode 512. The output of the sense amplifiers 626 and 628 are connected to a ventricular depolarization detector circuit 630 which is adapted to detect the occurrence of ventricular depolarizations in the first cardiac signal. In one embodiment, these components serve to sense near and/or far field ventricular cardiac signals and to amplify the signals indicating ventricular depolarizations, for example by sensing ventricular R-waves and or QRS-complexes, and apply signals indicative thereof to microprocessor 604. Among other things, the microprocessor 604 responds to the ventricular depolarization detector 630 by providing pacing signals to a pace output circuit 632 via bus 634, as needed according to the programmed pacing mode. In one embodiment, the pace output circuit 632 then provides output pacing signals to the ventricular electrode 528 and first defibrillation electrode 508 via terminals 610 and 612. The first defibrillation electrode 508, the second defibrillation electrode 512 and the housing 620 are also coupled to a cardioversion/defibrillation output circuit 650 to provide pulses of either cardioversion or defibrillation electrical energy to the terminals 610 or 608 and the housing 620 under the control of the microprocessor 604. Power to the ICD 600 is supplied by an electrochemical battery 654 that is housed within the ICD 600.

Sense amplifier 640 is coupled to the control circuitry 602, and is electrically coupled to terminal 614 and 616 to sense a cardiac signal between the atrial electrode 538 and the housing 620. In an alternative embodiment, a second atrial electrode (not shown) can be added to the atrial lead 536 and be coupled to sense amplifier 640 to allow for bipolar sensing and pacing. The output of the sense amplifier 640 is connected to an atrial depolarization detector 646 which is adapted to detect the occurrence of atrial depolarizations in a second cardiac signal. In one embodiment, these components serve to sense the second cardiac signal and to amplify the atrial depolarizations, for example by sensing atrial P-waves, and apply signals indicative thereof to microprocessor 604. Among other things, the microprocessor 604 can respond to the atrial depolarization detector 646 by providing pacing signals to the pace output circuit 632 via bus 634, as needed according to the programmed pacing mode. Pace output circuit 632 provides output pacing signals to terminals 614 and 616.

The control circuitry 602 further includes a cardiac data analyzing circuit 660, which is coupled to the ventricular depolarization detector circuit 630, the atrial depolarization detector circuit 646, the microprocessor 604 and the memory circuit 606 via bus 634. In one embodiment, the cardiac data analyzing circuit 660 analyzes ventricular depolarizations for the occurrence of a tachycardia episode. When a tachycardia episode is detected, the cardiac data analyzing circuit 660 analyzes the ventricular depolarizations in the first cardiac signal and the atrial depolarizations in the second cardiac signal to determine whether a one-to-one association of atrial depolarizations to ventricular depolarizations exists.

When a tachycardia episode having a one-to-one association of atrial depolarizations to ventricular depolarizations is detected, a cycle length interval circuit 664, coupled to the cardiac data analyzing circuit 660, is used to calculate both the first intervals between detected ventricular depolarizations in the first cardiac signal and first predetermined cardiac events and the second intervals between detected atrial depolarizations in the second cardiac signal and second predetermined cardiac events. In one embodiment, the cycle length interval circuit 664 locates the predetermined points on the sensed cardiac complexes from which the interval measurements are made. In one embodiment, the predetermined points are repeatably identifiable portions of the cardiac complex in the cardiac signal which have been programmed into the memory 606 of the ICD 600 for use in the cycle length interval circuit 664.

Once the intervals have been measured, the microprocessor 604 determines a first characteristic for a first predetermined series of the first intervals and a second characteristic for a second predetermined series the second intervals measured by the cycle length interval circuit. The microprocessor 604 then classifies the tachycardia episode as either occurring in an antegrade direction or a retrograde direction based on the first characteristic and the second characteristic.

In one embodiment, the microprocessor 604 calculates variance values (e.g., $\sigma^2(x)$, $\sigma^2(y)$) from the intervals measured by the cycle length interval circuit 664. The microprocessor 604 then calculates the variance values from predetermined series of measured intervals. For example, the microprocessor 604 is programmed to calculate the first variance value from the first predetermined series of the first intervals and to calculate the second variance value from the second predetermined series of the second intervals. The microprocessor 604 then compares the variance values and classifies the tachycardia episode as either occurring in an antegrade direction or a retrograde direction based on the values of the first variance and the second variance. In one embodiment, the microprocessor 604 classifies the tachycardia episode as occurring in an antegrade direction when the second variance is less than or equal to the first variance. Alternatively, the microprocessor 604 classifies the tachycardia episode as occurring in a retrograde direction when the second variance is greater than the first variance.

Electronic communication circuitry 668 is additionally coupled to the control circuitry 602 to allow the ICD 600 to communicate with an external controller 670. In one embodiment, the electronic communication circuitry 668 includes a data receiver and a data transmitter to send and receive and transmit signals and cardiac data to and from an external programmer 670. In one embodiment, the data receiver and the data transmitter include a wire loop antenna 672 to establish a radio frequency telemetric link, as is known in the art, to receive and transmit signals and data to and from the programmer unit 670.

What is claimed is:

1. A system, comprising:
   at least one cardiac lead including at least three electrodes;
   control circuitry coupled to the at least three electrodes, where the control circuitry receives a first cardiac signal which includes indications of ventricular depolarizations and a second cardiac signal which includes indications of atrial depolarizations, and where the control circuitry includes:
   a ventricular depolarization detector circuit to detect the occurrence of ventricular depolarizations in the first cardiac signal;
   an atrial depolarization detector circuit to detect the occurrence of atrial depolarizations in the second cardiac signal;
   a cardiac data analyzing circuit coupled to the ventricular depolarization detector circuit and the atrial depolarization detector circuit, where the cardiac data analyzing circuit analyzes ventricular depolarizations for the occurrence of a tachycardia episode, and when the tachycardia episode occurs the cardiac data analyzing circuit analyzes the ventricular depolarizations and the atrial depolarizations to determine whether a one-to-one association of atrial depolarizations to ventricular depolarizations exists;

a cycle length interval circuit coupled to the cardiac data analyzing circuit, where the cycle length interval circuit calculates both first intervals between detected ventricular depolarizations and first predetermined cardiac events and calculates second intervals between detected atrial depolarizations and second predetermined cardiac events when the cardiac data analyzing circuit detects the tachycardia episode having the one-to-one association of atrial depolarizations to ventricular depolarizations; and a microprocessor coupled to the cycle length interval circuit, where the microprocessor determines a first variability characteristic for a first predetermined series of the first intervals and a second variability characteristic for a second predetermined series of the second intervals and classifies the tachycardia episode as occurring in either an antegrade direction or a retrograde direction based on a comparison of the first variability characteristic and the second variability characteristic.

2. The system of claim 1, where the first predetermined cardiac events are subsequent ventricular depolarizations detected in the first cardiac signal by the ventricular depolarization detector circuit and the second predetermined cardiac events are subsequent atrial depolarizations detected in the second cardiac signal by the atrial depolarization detector circuit.

3. The system of claim 2, where the microprocessor determines a first variance for the first variability characteristic and a second variance for the second variability characteristic, and classifies the tachycardia episode based on the values of the first variance and the second variance.

4. The system of claim 3, where the cycle length interval circuit calculates atrial—atrial (AA)-intervals between a detected atrial depolarization and subsequently detected atrial depolarization, and calculates ventricular—ventricular (VV) intervals between a detected ventricular depolarization and subsequently detected ventricular depolarization; and the microprocessor determines the first variance for the VV-intervals and the second variance for the AA-intervals, where the microprocessor classifies the tachycardia episode as occurring in the antegrade direction when the second variance is less than or equal to the first variance.

5. The system of claim 3, where the microprocessor classifies the tachycardia episode as occurring in the retrograde direction when the second variance is greater than the first variance.

6. The system of claim 1, where the first predetermined cardiac events are subsequent atrial depolarizations detected in the second cardiac signal by the atrial depolarization detector circuit and the second predetermined cardiac events are subsequent ventricular depolarizations detected in the first cardiac signal by the ventricular depolarization detector circuit.

7. The system of claim 6, where the microprocessor determines a first variance for the first variability characteristic and a second variance for the second variability characteristic, and classifies the tachycardia episode based on the values of the first variance and the second variance.

8. The system of claim 7, where the cycle length interval circuit calculates atrial-ventricular (AV)-intervals between a detected atrial depolarization and subsequently detected ventricular depolarization, and calculates ventricular-atrial (VA)-intervals between a detected ventricular depolarization and subsequently detected atrial depolarization; and the microprocessor determines the first variance for the VA-intervals and the second variance for the AV-intervals, where the microprocessor classifies the tachycardia episode as occurring in the antegrade direction when the second variance is less than or equal to the first variance.

9. The system of claim 8, where the microprocessor classifies the tachycardia episode as occurring in the retrograde direction when the second variance is greater than the first variance.

10. The system of claim 1, where the first predetermined series includes a number of first intervals and the second predetermined series includes the number of second intervals and the number is a programmable value of at least five (5) which is stored in the microprocessor.

11. A method, comprising:

detecting atrial depolarizations and ventricular depolarizations;

detecting a tachycardia episode from the ventricular depolarizations, where the tachycardia episode has a one-to-one association of atrial depolarizations to ventricular depolarizations;

during the tachycardia episode that has the one-to-one association of atrial depolarizations to ventricular depolarizations, measuring first intervals between the ventricular depolarizations and first predetermined cardiac events and second intervals between the atrial depolarizations and second predetermined cardiac events; and classifying the tachycardia episode based on a comparison of variability characteristics of a series of the first intervals and a series of the second intervals; and where classifying the tachycardia episode includes calculating a first interval characteristic from the first intervals and a second interval characteristic from the second intervals; and where calculating the first interval characteristic includes calculating a first variance value from the first intervals, calculating the second interval characteristic includes calculating a second variance value from the second intervals, and classifying the tachycardia episode includes classifying the tachycardia episode based on the first variance value and the second variance value; and where the first predetermined cardiac events are subsequent ventricular depolarizations and the second predetermined cardiac events are subsequent atrial depolarizations, where measuring the first intervals includes calculating ventricular—ventricular (VV)-intervals between the detected ventricular depolarizations and subsequently detected ventricular depolarizations, and measuring the second intervals includes calculating atrial—atrial (AA)-intervals between the detected atrial depolarizations and subsequently detected atrial depolarizations; and where classifying the tachycardia episode includes classifying the tachycardia episode as an antegrade rhythm when the second variance is less than or equal to the first variance.

12. The method of claim 11, where classifying the tachycardia episode includes classifying the tachycardia episode as a retrograde rhythm when the second variance is greater than the first variance.

13. A method, comprising:
  detecting atrial depolarizations and ventricular depolarizations;
  detecting a tachycardia episode from the ventricular depolarizations, where the tachycardia episode has a one-to-one association of atrial depolarizations to ventricular depolarizations;
  during the tachycardia episode that has the one-to-one association of atrial depolarizations to ventricular depolarizations, measuring first intervals between the ventricular depolarizations and first predetermined cardiac events and second intervals between the atrial depolarizations and second predetermined cardiac events; and
  classifying the tachycardia episode based on a comparison of variability characteristics of a series of the first intervals and a series of the second intervals; and
  where classifying the tachycardia episode includes calculating a first interval characteristic from the first intervals and a second interval characteristic from the second intervals; and
  where calculating the first interval characteristic includes calculating a first variance value from the first intervals calculating the second interval characteristic includes calculating a second variance value from the second intervals, and classifying the tachycardia episode includes classifying the tachycardia episode based on the first variance value and the second variance value; and
  where the first predetermined cardiac events are subsequent atrial depolarizations and the second predetermined cardiac events are subsequent ventricular depolarizations, where measuring the first intervals includes calculating ventricular-atrial (VA)-intervals between the detected ventricular depolarizations and subsequently detected atrial depolarizations, and measuring the second intervals includes calculating atrial-ventricular (AV)-intervals between the detected atrial depolarizations and subsequently detected ventricular depolarizations; and
  where classifying the tachycardia episode includes classifying the tachycardia episode as an antegrade rhythm when the second variance is less than or equal to the first variance.

14. The method of claim 13, where classifying the tachycardia episode includes classifying the tachycardia episode as a retrograde rhythm when the second variance is greater than the first variance.

15. A method comprising:
  receiving a first cardiac signal;
  receiving a second cardiac signal;
  detecting a tachycardia episode based on the first cardiac signal and the second cardiac signal;
  selecting a first series of intervals based on predetermined features in the first cardiac signal and the second cardiac signal;
  selecting a second series of intervals based on predetermined features in the first cardiac signal and the second cardiac signal;
  determining a first characteristic based on variability of the first series;
  determining a second characteristic based on variability of the second series;
  comparing the first characteristic with the second characteristic; and
  classifying the tachycardia episode based on the comparison; and
  wherein classifying the tachycardia episode includes classifying the tachycardia episode as an antegrade direction tachycardia episode when the first characteristic has a value greater than the second characteristic.

* * * * *

UNITED STATES PATENT AND TRADEMARK OFFICE
CERTIFICATE OF CORRECTION

PATENT NO. : 7,203,535 B1
APPLICATION NO. : 09/417558
DATED : April 10, 2007
INVENTOR(S) : Hsu et al.

It is certified that error appears in the above-identified patent and that said Letters Patent is hereby corrected as shown below:

On the face page, in field (56), under "Other Publications", in column 2, line 2, delete "1998.*" and insert -- 1998; A61N 1/368.* --, therefor.

On the face page, in field (57), under "Abstract", in column 2, lines 1–15, delete "An implantable cardioverter/defibrillator includes a tachycardia detection system that detects one-to-one (1:1) tachycardia, which is a tachycardia with a one-to-one relationship between atrial and ventricular contractions. When the 1:1 tachycardia is detected, the system discriminates ventricular tachycardia (VT) from supraventricular tachycardia (SVT) based on analysis of a cardiac time interval. Examples of the cardiac time interval include an atrioventricular interval (AVI) and a ventriculoatrial interval (VAI). A template time interval is created during a known normal sinus rhythm. The system measures a tachycardia time interval after detecting the 1:1 tachycardia, and indicates a VT detection if the tachycardia time interval differs from the template time interval by at least a predetermined percentage of the template time interval." and insert -- A system and method for discriminating cardiac rhythms occurring in an antegrade direction from cardiac rhythms occurring in a retrograde direction. Atrial depolarizations and ventricular depolarizations are sensed. When a tachycardia episode having a one-to-one association of atrial depolarizations to ventricular depolarizations is detected, first intervals between the ventricular depolarizations and first predetermined cardiac events and second intervals between the atrial depolarizations and second predetermined cardiac events are measured. Characteristics of the first and second intervals are then used to classify the tachycardia episode as either an antegrade rhythm or a retrograde rhythm. --, therefor.

In column 17, line 27, in Claim 13, after "intervals" insert -- , --.

Signed and Sealed this

Eighteenth Day of December, 2007

JON W. DUDAS
*Director of the United States Patent and Trademark Office*